(12) United States Patent
Harbron

(10) Patent No.: US 6,423,492 B1
(45) Date of Patent: Jul. 23, 2002

(54) HYBRIDIZATION ASSAY FOR DETECTING A SINGLE-STRANDED TARGET NUCLEIC ACID IN WHICH EXCESS PROBE IS DESTROYED

(75) Inventor: Stuart Harbron, Berkhamsted (GB)

(73) Assignee: Zetatronics Limited, London (GB)

( * ) Notice: Subject to any disclaimer, the term of this patent is extended or adjusted under 35 U.S.C. 154(b) by 0 days.

(21) Appl. No.: 09/403,105

(22) PCT Filed: Apr. 9, 1998

(86) PCT No.: PCT/GB98/01057

§ 371 (c)(1),
(2), (4) Date: Oct. 14, 1999

(87) PCT Pub. No.: WO98/46790

PCT Pub. Date: Oct. 22, 1998

(30) Foreign Application Priority Data

Apr. 14, 1997 (GB) .............................................. 9707531

(51) Int. Cl.[7] .......................... C12Q 1/68; C12N 9/22; C12N 1/20; C12P 19/34; C07A 21/02; C07H 21/04

(52) U.S. Cl. ........................ 435/6; 435/199; 435/252.3; 435/91.21; 435/91.2; 536/22.1; 536/23.1; 536/24.3; 536/24.33

(58) Field of Search ............................ 435/6, 810, 91.1, 435/91.2, 91.31, 91.21, 252.3, 193, 252.33, 199; 536/22.1, 24.3, 24.33, 23.1, 25.3

(56) References Cited

U.S. PATENT DOCUMENTS

| 4,833,084 A | | 5/1989 | Carrico .................. 435/240.27 |
| 5,200,313 A | * | 4/1993 | Carrico ........................... 435/6 |
| 5,536,648 A | * | 7/1996 | Kemp et al. ................ 435/91.2 |
| 5,627,030 A | * | 5/1997 | Pandian et al. ................. 435/6 |
| 6,027,886 A | * | 2/2000 | Leying et al. .................. 435/6 |

FOREIGN PATENT DOCUMENTS

| EP | 0 135 159 A2 | | 3/1985 |
| EP | 0 144 913 A2 | | 6/1985 |
| EP | 0 405 592 A2 | | 1/1991 |
| EP | 0 462 353 A1 | | 12/1991 |
| EP | 0 780 479 A2 | | 12/1996 |
| GB | 2 324 370 B | | 10/1998 |
| WO | WO 90/01559 | * | 2/1990 |
| WO | WO 90/01559 A1 | | 2/1990 |
| WO | WO 98/19168 A1 | | 5/1998 |
| WO | PCT/GB 98/01057 | | 9/1998 |

OTHER PUBLICATIONS

Steffan et al. Solution Hybridization Assay for detecting genetically engineered microorganisms in environmental samples. Bio Techniques. vol. 8, No. 3, pp. 316–318, Jan. 1990.*

Ahern, H. Biochemical, Reagent Kits offer Scientists Good Return on Investment. The Scientist. vol. 9, No. 15, pp. 1–5, Apr. 1995.*

Corey et al. Strand Invasion by Oligonucleotide–Nuclease Conjugates. Bioconjugate Chemistry, vol. 6, pp. 93–100, Feb. 1995.*

Derwent, Gene Defect Method Comprise Gene Extract Denature Single Strand Specific Bond Label Gene Probe React, Analytical Biochemistry, Aug. 5, 1992, 1 page, DW9225 C12Q1/68.

Stuart Harbron, Jenny J. Eggelte, Mark Fisher & Brian Rabin, Amplified Assay of Alkaline Phosphafase Using Flavinadenine Dinucleotide Phosphate as Substrate, Analytical Biochemistry, May 13, 1992, pp. 119–124, vol. 206.

Core Dr, Munoz–Medellin D, Huang A, Strand invations by oligonucleotide—nuclease conjugates, National Library of Medicine, PubMed, 1995 Jan–Feb;6(1):93–100.

* cited by examiner

Primary Examiner—Stephanie W. Zitomer
Assistant Examiner—Cynthia B. Wilder
(74) Attorney, Agent, or Firm—Hopgood, Calimafde, Judlowe & Mondolino

(57) ABSTRACT

A method is disclosed for detecting single-stranded target nucleic acid (2) which comprises the steps of forming a hybrid between said target nucleic acid and a nucleic acid probe (4), said nucleic acid probe labelled with an enzyme reagent (6) which hydrolyses single-stranded nucleic acid but is substantially without effect on double-stranded nucleic acid, said hybrid formed under conditions of pH which are outside the activity range of said enzyme reagent, adjusting said pH to a value within the activity range of said enzyme reagent allowing said enzyme reagent substantially to hydrolyse any single-stranded nucleic acid present, and detecting said hybrid.

57 Claims, 1 Drawing Sheet

HYBRIDIZATION ASSAY FOR DETECTING A SINGLE-STRANDED TARGET NUCLEIC ACID IN WHICH EXCESS PROBE IS DESTROYED

TECHNICAL FIELD

This invention relates to methods for detecting nucleic acids.

BACKGROUND ART

Nucleic acid hybridisation is a widely used technique for identifying, detecting and quantitating target polynucleotide sequences in a sample. This technique relies for its success on complementary base pairing between the two halves of a double-stranded nucleic acid molecule: when single-stranded nucleic acids are incubated in solution under suitable conditions of temperature, pH and ionic strength, complementary base sequences pair to form double-stranded stable hybrid molecules. This ability of single-stranded nucleic acid molecules to form a hydrogen-bonded structure with their complementary nucleic acid sequences has long been employed as an analytical tool in recombinant DNA research.

In most cases the sample will contain double-stranded nucleic acid and must be denatured prior to the hybridisation assay to render it single-stranded. A nucleic acid having a known sequence which is complementary to the target sequence is either synthesised chemically in an automated fashion with great facility, or is isolated from the appropriate organism and rendered single-stranded by denaturation. It is then used as a probe to search a sample for a target complementary sequence. Detection of specific target nucleic acids enables accurate diagnosis of bacterial, fungal and viral disease states in humans, animals and plants. Additionally, the ability to probe for a specific nucleotide sequence enables the diagnosis of human genetic disorders. Hybridisation produces stable hybrids, and a number of different approaches are known to the art for detecting these.

One approach involves the use of labelled probes. By labelling a probe nucleic acid with some readily detectable chemical group, it is possible to detect the polynucleotide sequence of interest in a test medium containing sample nucleic acids in single-stranded form. Nucleic acids have been labelled with radioisotopes, enzymes and fluorescent molecules. The use of labelled nucleic acids as probes in macromolecuiar analysis is important for clinical, veterinary and environmental diagnostic applications.

Early methods for detecting target nucleic acids involved their immobilisation on a solid support such as nitrocellulose paper, cellulose paper, diazotized paper, or a nylon membrane. For example, in U.S. Pat. No. 4,358,535 to Falkow a method is disclosed in which the target nucleic acid is rendered single-stranded and then immobilised onto a membrane. A labelled probe which is complementary to the target nucleic acid is brought into contact with the solid support and hybridises to the target nucleic acid. The solid support is washed several times at a carefully controlled temperature to remove unbound and non-specifically bound probe without removing specifically bound probe, and the presence of the label in the resulting hybrid is determined. A disadvantage of this method is that it is neither easy nor convenient to attach the single-stranded target nucleic acid to a solid support, the whole process involving a 12–15 hour incubation of the nucleic acid with a nitro-cellulose sheet, followed by a 2 hour baking step. This makes the assay slow and unattractive for routine use. It is also cumbersome, with the hybridisation and washing steps being carried out in a sealed pouch, containing the membrane and the buffer solution. In addition, when very low concentrations must be detected, the ratio of specific to non-specificaily bound probe can be very low and repeated washing under highly stringent conditions is frequently required. Under these conditions the sensitivity of the assay is often compromised because of substantial loss of specifically bound probe.

Since then a many improvements have been made, most of which employ a sandwich approach using two probes: a reporter probe and a capture probe. The reporter probe is a nucleic acid having a sequence complementary to at least part of the target sequence and which is labelled with a detectable group. The capture probe is a nucleic acid having a sequence complementary to at least part of the target sequence, but which is different to that of the reporter probe, and which is labelled with an immobilisable group. In many applications, pairs of specific binding members (sbm's) have been used for this purpose.

For example, in U.S. Pat. No. 5,273,882 to Snitman and Stroupe a capture probe complementary to part of the target nucleic acid is labelled with an antigen or antibody. After hybridisation between this capture probe and the target, the solution is introduced to a support-bound antibody or antigen which immobilises the hybrid formed between the capture probe and the target. Following a washing step, a second, reporter probe, complementary to a different region of the target nucleic acid, is introduced and the triple sandwich formed is detected.

Similar approaches are described by Holtke et al.: in U.S. Pat. No. 5,344,757 is disclosed a method in which a reporter probe is labelled with digoxin or digoxygenin, and hybrids are captured using antibodies against this hapten. In this case, a capture probe is not used, and the method is limited either to the detection of an immobilised target, or when the assay is used for detecting PCR products, one of the primers is immobilised. In U.S. Pat. No. 5,354,657 the method is further developed and involves the solution hybridisation between the target nucleic acid and a reporter probe labelled with digoxin or digoxygenin. This hybrid is captured by a solid-supported capture probe, complementary to a different region of the target. A detectably labelled antibody against the hapten is then added and the hybrids formed detected.

Specific binding members other than antigens or haptens and antibodies have been used. In U.S. Pat. No. 5,374,524 to Miller is described a method for the solution sandwich hybridisation, capture and detection of amplified nucleic acids. Amplicons are denatured and treated with an enzyme-labelled reporter probe and a biotinylated capture probe. Hybrids formed are captured using streptavidin-coated chromium dioxide particles.

Disadvantages of these approaches include the increased cost and complexity of using two probes. For example, for each assay two probes need to be synthesised and labelled: one for use as the capture probe, and the other for use as a reporter probe. In addition, hybridisation conditions have to be carefully chosen to form the sandwich of target, capture probe and reporter probe.

Simpler approaches which avoid the use of a capture probe have been described. Atlas and Steffan (*Biotechniques* (1990) 8:316–318) disclose a solution hybridisation method for detecting genetically-engineered micro-organisms in environmental samples. The detection method involves recovery of DNA from the microbial community of an environmental sample followed by hybridisation in solution with a radio-labelled RNA gene probe. After nuclease digestion of non-hybridised probe RNA, the DNA-RNA hybrids formed in the solution hybridisation are separated by column chromatography and detected by liquid scintillation counting. A less cumbersome approach is disclosed in U.S. Pat. No. 4,978,608 to Kung and Nagainis in which DNA is detected in a sequence non-specific manner using a high affinity single-stranded DNA-binding protein. This approach is extended in U.S. Pat. No. 5,536,648 to Kemp et al. who disclose an amplified DNA assay using a double stranded DNA binding protein. The method uses a PCR primer having a nucieotide sequence which is a ligand for a double stranded DNA-binding protein. After amplification the amplified target is captured by the double stranded DNA-binding protein immobilised on a solid surface. This method does not use a capture probe and will detect any amplification product containing the sequence which is a ligand for the double stranded DNA-binding protein. A disadvantage of this approach is that it relies an the accuracy of the amplification step for its specificity.

Another method is disclosed in U.S. Pat. No. 4,968,602 to Dattagupta. The test sample is modified chemically to introduce a reactive site. This mixture is then contacted with a reporter probe. After a solution phase hybridisation step, the hybrid is brought into contact with a surface having an immobilised reaction partner which reacts with the reactive site, and allows the unhybridised material to be washed away. A disadvantage of this approach is that the initial reaction step may interfere with the subsequent formation of the hybrid.

A further approach in which the hybrid itself is a hapten and which therefore only requires one probe is described by Carrico. In U.S. Pat. No. 4,743,535 is disclosed a nucleic acid hybridisation assay involving a reporter probe which results in the formation of a hybrid having epitopes for an antibody reagent. The antibody reagent is selective for DNA-RNA or RNA-RNA hybrids over the single-stranded nucleic acids. U.S. Pat. No. 5,200,313 to Carrico further discloses a nucleic acid hybridisation assay employing an immobilised or immobilisable polynucleotide probe selected to form DNA-RNA or RNA-DNA hybrids with the particular polynucleotide sequence to be determined. Resulting hybrids are detected by binding of an antibody reagent, preferably labelled with a detectable chemical group, selective for binding the hybrids in the presence of the single-stranded sample and probe nucleic acids.

Advantageous feature of Carrico's inventions are that no immobilisation or labelling of sample nucleic acids is required and hybridisation can be performed entirely in solution. A further advantage is that a universal detection reagent may be used whatever the target is.

The key feature of Carrico's invention is the requirement for antibodies specific for double-stranded hybrids having little affinity for single-stranded nucleic acid. The generation of specific polyclonal antibodies that will bind double-stranded nucleic acid but not single-stranded nucleic acid is complicated by the fact that polyclonal antisera may contain antibodies that will cross-react with single-stranded nucleic acid. Polyclonal antisera may also contain naturally occurring antibodies to single-stranded nucleic acid or antibodies to single-stranded nucleic acid arising as a result of the immunisation. Monoclonal antibody technology can provide a means to select an antibody with desired affinity and specificity which will overcome in part these problems. Such monoclonal antibodies which will selectively bind double-stranded DNA (U.S. Pat. No. 4,623,627) or DNA-RNA hybrids (U.S. Pat. No. 4,833,084 to Carrico) have been prepared. Monoclonal antibodies are however more expensive to produce and generally have lower affinities than polyclonal antibodies.

The monoclonal antibodies disclosed by Carrico (U.S. Pat. No. 4,833,084) are specific for DNA-RNA duplexes, particularly DNA-RNA heteropolymer duplexes, and are characterised by having cross-reactivity for binding to single or double-stranded DNA or RNA, as measured by competitive immunoassay, of less than about 1:1000, and preferably less than 1:10,000, and an affinity for DNA-RNA heteropolymer duplexes greater than $10^9$ L/mol.

Chevrier et al. (*Molecular and Cellular Probes* (1993) 7: 137–197) report that up to 200 fmol of a capture probe may be attached to Covalink NH microwells (Nunc). The antibodies disclosed by Carrico would therefore have a lower detection limit of approximately $\frac{1}{10,000}$ of 200 fmol, or 20 amol. In addition non-specific binding between the labelled antibody and the surface on which the probe is immobilised will also contribute to a background signal. Carrico's method is thus not applicable to the detection of very low concentrations of target nucleic acid which are in the range of sensitive detection systems such as signal amplification detection systems or chemiluminescence. The approach of Carrico finds utility in the detection of target amplification products, such as those generated by the polymerase chain reaction (PCR). For example, a commercial assay, GEN-ETI-K™, from Sorin utilises probes immobilised on microtitre plates by means of a streptavidin-biotin bridge and antibodies against double stranded DNA labelled with peroxidase. Its chief application is in the assay of nucleic acid amplification products.

One approach to overcome the problem of cross-reactivity is disclosed in U.S. Pat. No. 5612,458 to Hyldig-Nielson and Pluzek They use antibodies to complexes between peptide nucleic acid (PNA) and nucleic acids, particularly antibodies to nucleic acid probe-DNA or nucleic acid probe-RNA hybrids.

Another approach is to attempt to improve the affinity or selectivity of the antibody used. Fliss et al. (*Applied and Environmental Microbiology* (1993) 59:2698–2705) disclose murine monoclonal antibodies specific for DNA-RNA hybrids which are used to detect Lysteria DNA-RNA hybrids formed in solution from a biotinylated gene probe and rRNA extracted from Lysteria. They also teach that the endonuclease digestion approach used by Atlas and Stefan (see above) does not efficiently separate hybridised from unhybridised molecules. Significantly, they do not teach that treatment with a nuclease to remove any single-stranded nucleic acids prior to capture with the murine monoclonal antibodies specific for DNA-RNA hybrids would offer an improvement to their assay.

In summary, Carrico discloses a simple method for capturing hybrids formed in solution between a target nucleic acid and a nucleic acid probe which utilises antibodies specific for double-stranded nucleic acid. A disadvantage of this approach is the cross-talk between antibody and any single-stranded nucleic acid which may be present. This limits the sensitivity of the assay. Atlas and Steffan disclose another solution phase hybridisation assay in which hybrids are separated by column chromatography following an endonuclease digestion step. A similar approach is utilised in nuclease protection assays. This is a sensitive technique for the detection, quantitation, and characterisation of RNA. The hybridisation reaction occurs in solution allowing complete hybridisation of the probe to the target mRNA.

After hybridisation, remaining single-stranded probe RNA and unhybridised sample RNA are removed by digestion with a mixture of ribonucieases A and T1, or S1 nuclease. Then, in a single step, the nucleases are inactivated and the remaining hybrids precipitated. Nuclease protection assays are not used for the detection of DNA. A disadvantage of these latter two methods is that they are cumbersome and do not accurately quantify the amount of target nucleic acid present.

There remains a need to combine the advantageous features of Carrico's invention with one having reduced crosstalk, lower background and improved sensitivity.

In U.S. Pat. Nos. 4,683,195 and 4,683,202, DNA or RNA is amplified by the polymerase chain reaction (PCR). These patents are incorporated herein by reference in their entirety. This method involves the hybridisation of an oligonucleotide primer to the 5' end of each complementary strand of the double-stranded target nucleic acid. The primers are extended from the 3' end in a 5'→3' direction by a DNA polymerase which incorporates free nucleotides into a nucleic acid sequence complementary to each strand of the target nucleic acid. After dissociation of the extension products from the target nucleic acid strands, the extension products become target sequences for the next cycle. In order to obtain satisfactory amounts of the amplified DNA, repeated cycles must be carried out, between which cycles, the complementary DNA strands must be denatured under elevated temperatures.

A method of detecting a specific nucleic acid sequence present in low copy in a mixture of nucleic acids, called ligase chain reaction (LCR), has also been described. WO 89/09835 describes this method and is incorporated herein by reference in its entirety. Target nucleic acid in a sample is annealed to probes containing contiguous sequences. Upon hybridisation, the probes are ligated to form detectable fused probes complementary to the original target nucleic acid. The fused probes are disassociated from the nucleic acid and serve as a template for further hybridisation's and fusions of the probes, thus amplifying geometrically the nucleic acid to be detected. The method does not use DNA polymerase.

Other known nucleic acid amplification procedures include transcription-based amplification systems (Kwoh et al., *Proc. Natl. Acad. Sci. (U.S.A.)* (1989) 86:1173; Gingeras et al., WO 88/10315; Davey et al., EP 329,822; Miller et al., WO 89/06700), RACE (Frohman, In: PCR Protocols: A Guide to Methods and Applications, Academic Press, NY (1990)) and one-sided PCR (Ohara, et al., *Proc. Natl. Acad. Sci. (U.S.A.)* (1989) 86:5673–5677). Particularly suitable amplification procedures include Nucleic Acid Sequence-Based Amplification, Strand Displacement Amplification, and Cycling Probe Amplification.

Methods based on ligation of two (or more) oligonucleotides in the presence of nucleic acid having the sequence of the resulting di-oligonucleotide, thereby amplifying the di-oligonucleotide, are also known (Wu et al., *Genomics* (1989) 4:560).

An isothermal amplification method has been described in which restriction endonucleases and ligases are used to achieve the amplification of target molecules that contain nucleotide 5'-[a-thio]triphosphates in one strand of a restriction site (Walker et al., *Proc. Natl. Acad. Sci. (U.S.A.)* (1992) 89:392–396).

It is important that enzymes employed as labels catalyse a reaction which has an easily detectable product, and have a high turnover number to allow sensitive detection: horseradish peroxidase and alkaline phosphatase are most common. Although sensitive chemiluminometric assays for horseradish peroxidase have been described which allow small amounts of enzyme to be detected, problems associated with its use include lack of enzyme and substrate stability and the presence of endogenous peroxidases in samples.

For alkaline phosphatase, enzyme amplification cycles have been described which further reduce the amount of enzyme which can be detected, thereby extending the detection limit. In one method, the amplification system comprises an apoenzyme which is convertible into a holoenzyme by interaction with an accessory subunit and a masked form of the subunit which is convertible into its active unmasked form by the action of the enzyme to be detected. For example, in U.S. Pat. No. 5,445,942 to Rabin et al., a method is disclosed for detecting a hydrolase enzyme able to hydrolyse a synthetic derivative of FAD substituted in such a way that it yields FAD when hydrolysed, and is incorporated herein by reference in its entirety. Here the subunit is FAD and the masked form is 3'FADP, and the apoenzyme is apoglucose oxidase or apo-D-aminoacid oxidase.

The FAD produced forms an active holoenzyme from the corresponding apoenzyme. This approach allows the detection of small amounts of alkaline phosphatase in short periods of time. For example, using such an amplification system in which the apoenzyme is apo-D-amino acid oxidase has permitted the detection of 0.1 amol of alkaline phosphatase in less than 30 minutes (Harbron et al., *Anal. Biochem.* (1992) 206: 119–124). In GB9622524.8 this approach is further extended to an amplification assay for nuclease $P_1$, and is incorporated herein by reference in its entirety.

DISCLOSURE OF INVENTION

Broadly, the present invention combines advantageous aspects of the above techniques and discloses a new and improved method for detecting single-stranded target nucleic acid comprising the steps of:

(a) forming a hybrid between said target nucleic acid and a nucleic acid probe, said nucleic acid probe labelled with an enzyme reagent which hydrolyses single-stranded nucleic acid but is substantially without effect on double-stranded nucleic acid, said hybrid formed under conditions of pH which are outside the activity range of said enzyme reagent, (b) adjusting said pH to a value within the activity range of said enzyme reagent, (c) allowing said enzyme reagent substantially to hydrolyse any single-stranded nucleic acid present, and (d) detecting said hybrid.

In a further aspect, the invention provides a variety of means for detecting the hybrid by means of a hybrid-binding reagent such as an antibody or DNA-binding protein specific for double-stranded nucleic acid, or by means of a pair or pairs of sbm's. These may be a antigen or hapten and the corresponding antibody, biotin and avidin, streptavidin or neutravidin, or a nucleic acid binding protein specific for a sequence present in the nucleic acid probe. Any of these agents may be labelled with a detectable label which may an enzyme, a fluorescent moiety, a chemiluminescent moiety, an electro-chemiluminescent moiety or a coloured moiety.

In a further aspect the invention discloses a method for detecting DNA-RNA hybrids, DNA-DNA, RNA-RNA, DNA-RNA or DNA-PNA hybrids between a target nucleic acid and a nucleic acid probe having a sequence complementary to part of the target nucleic acid.

In a another further aspect the invention discloses a method for detecting hybrids between nucleic acid amplification products and a nucleic acid probe having a sequence complementary to part of the amplified nucleic acid.

In a further aspect the invention discloses a method for detecting hybrids between target nucleic acid extracted from a clinical specimen, a veterinary specimen, a food specimen or an environmental sample and a nucleic acid probe having a sequence complementary to part of the target nucleic acid.

In a another further aspect the invention discloses a method for the detection of multiple nucleic acid targets in a sample.

In further aspects the invention provides a kit for carrying out the method.

Preferred embodiments of the invention may enable one to achieve one or more of the following objects and advantages:

(a) to provide a method for detecting hybrids between a target nucleic acid and a nucleic acid probe having a sequence complementary to part of the target nucleic acid by means of a specific binding member, in which any single-stranded nucleic acid is removed by treatment with an enzyme reagent attached to said probe and which is specific for single-stranded nucleic acids. Advantages of the present invention are: only a single probe is required; highly sensitive detection systems, such as chemiluminescence or enzyme amplification cascades may be used to detect the hybrids; and the sensitive detection of target nucleic acid may be achieved without using target amplification techniques, such as PCR or LCR.

(b) to provide a method for detecting multiple nucleic acid targets. An advantage of the present invention is that a single sample may be screened for a number of targets, thereby increasing the speed of assay and reducing the number of sample which are required.

(c) to provide a universal method for detecting target nucleic acid. An advantage of the present invention is that it may be used with existing nucleic acid probes and their corresponding detection systems.

(d) to provide a method for detecting hybrids between DNA-RNA, RNA-DNA, RNA-RNA, RNA-PNA and DNA-PNA hybrids by appropriate selection of the hybrid binding reagent and enzyme reagent used.

REFERENCE NUMERALS USED IN THE DRAWINGS

Figure 1:
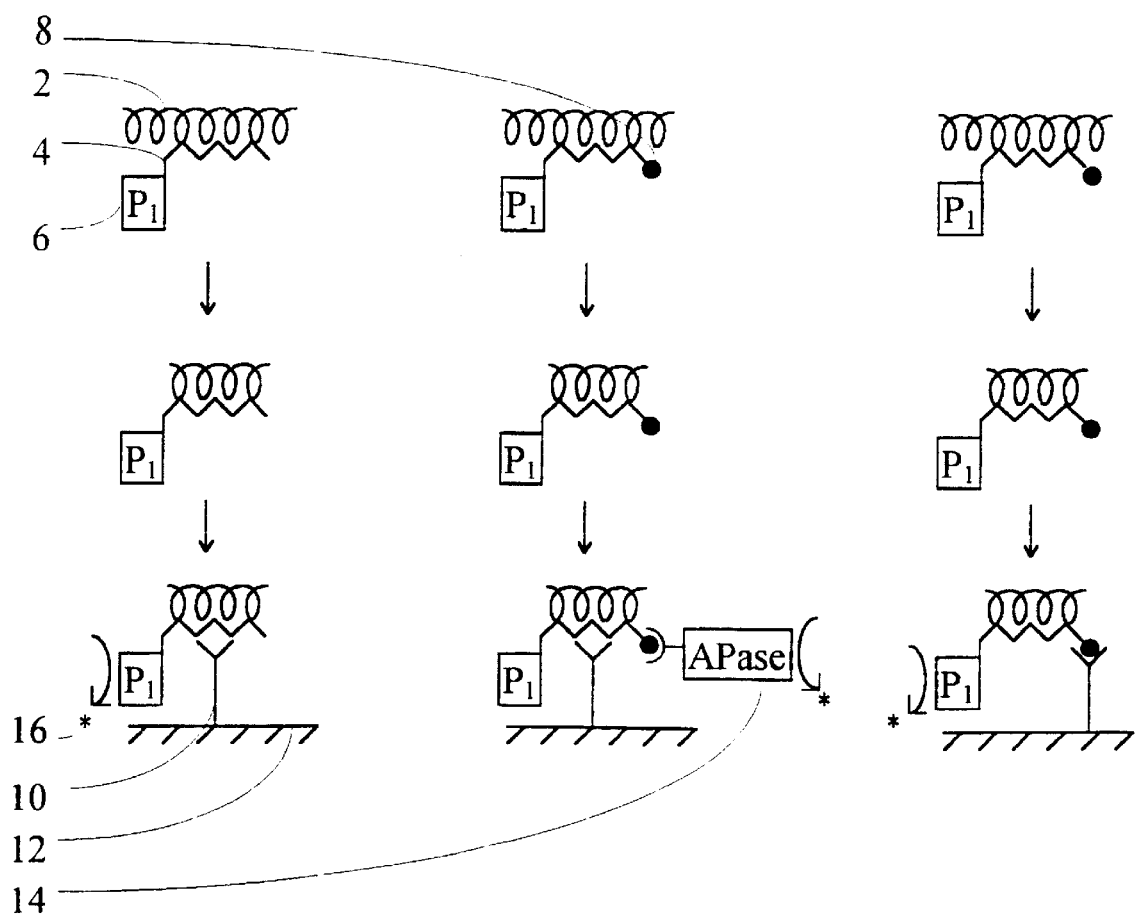
FIG. 1 is a diagrammatic representation of three preferred embodiments of the present invention for the detection of single-stranded nucleic acids.

2—single-stranded target nucleic acid
4—nucleic acid probe
6—enzyme reagent
8—first member of a specific binding pair
10—specific binding member
12—solid surface
14—second member of a specific binding pair
16—product

BEST MODES FOR CARRYING OUT THE INVENTION

The present invention provides a method for detecting hybrids between a target nucleic acid and a nucleic acid probe having a sequence complementary to part of the target nucleic acid by treating the sample with an enzyme reagent to remove single-stranded nucleic acids, and detecting the hybrid.

The target nucleic acid may be DNA or RNA, and is obtained from any medium of interest, for example, a liquid sample of medical, veterinary, environmental, or industrial significance. The target nucleic acid may also be the product of a nucleic acid amplification assay, such as PCR or LCR. If the target nucleic acid is principally double stranded, it will be treated to denature it prior to the formation of the hybrid. Denaturation of nucleic acids is preferably accomplished by heating in boiling water or alkali treatment (e.g., 0.1 N sodium hydroxide), which if desired, can simultaneously be used to lyse cells. Also, release of nucleic acids from cellular or viral sources can, for example, be obtained by mechanical disruption (freeze/thaw, abrasion, sonication), physical/chemical disruption (detergents such as Triton™, Tween, or sodium dodecylsulfate, alkali treatment, osmotic shock, or heat), or enzymatic lysis (lysozyme, proteinase K, pepsin). The resulting test medium will contain the target nucleic acid in single-stranded form.

The nucleic acid probe may be a DNA probe an RNA probe, or a PNA probe. The nucleic acid probe will comprise at least one single-stranded base sequence substantially complementary to at least part of the target nucleic acid sequence. However, such base sequence need not be a single continuous polynucleotide segment, but can be comprised of two or more individual segments interrupted by non-complementary sequences. These non-hybridisable sequences are linear. in addition, the complementary region of the nucleic acid probe can be flanked at the 3'- and 5'-termini by non-hybridisable sequences, such as those comprising the DNA or RNA of a vector into which the complementary sequence had been inserted for propagation. In either instance, the nucleic acid probe as presented as an analytical reagent will exhibit detectable hybridisation at one or more points with target nucleic acids of interest. The nucleic acid probe sequence can be of any convenient or desired length, ranging from as few as a dozen to as many as 10,000 bases, and including oligonucleotides having less than about 50 bases. The nucleic acid probe may be an oligonucleotide produced by solid-phase chemistry by a nucleic acid synthesiser. The RNA or DNA probe can be obtained in a variety of other conventional manners. It should be understood that in using the expressions RNA probe and DNA probe herein, it is not implied that all nucleotides comprised in the probe be ribonucleotides or 2'-deoxyribonucleotides. Therefore, one or more of the 2'-positions on the nucleotides comprised in the probe can be chemically modified provided the antibody binding characteristics necessary for performance of the present assay are maintained to a substantial degree. Likewise, in addition or alternatively to such limited 2'-deoxy modification, the nucleic acid probe can have in general any other modification along its ribose phosphate backbone provided there is no substantial interference with the specificity of the antibody to the double stranded hybridisation product compared to its individual single strands. In preferred embodiments, in addition to the enzyme label, the nucleic acid probe is labelled with either a detectable moiety or an immobilisable moiety. For example, the nucleic acid probe is prepared by solid-phase chemistry using a nucleic acid synthesiser and has a trityl-hexyl thiol derivatised 5'-end. The covalent attachment of the label to this moiety may be achieved by a number of well-known methods using a wide range of heterobifunctional reagents. For example, the method of Carlsson et al. *Biochem J* (1978) 173: 723–737) may be used: the label is reacted with 3-[(2)-pyridyldithio]propionic acid N-hydroxysuccinimide ester (SPDP) to give a 2-pyridyl disulphide-activated label. This allows disulphide exchange with trityl-hexyl thiol derivatised described above to yield a labelled nucleic acid probe. Other approaches for labelling the nucleic acid probe will be apparent to one skilled in the art. Additionally, a wide range of labelled nucleic acids is available from commercial sources. Preferred labels include the enzymes alkaline phosphatase, peroxidase, β-galactosidase, nuclease $P_1$ and nuclease $S_1$; the haptens digoxin, digoxygenin, fluorescein, fluorescein isothiocyanate, and biotin or biotin analogues.

A preferred embodiment of the present invention employs a nuclease as the enzyme reagent. A number of nucleases are known which are specific for single-stranded nucleic acids. For example, ribonuclease A and ribonuclease $T_1$ may be used in combination to hydrolyse single-stranded RNA. Other preferred nucleases include exodeoxyribonuclease I (E.C. 3.1.11.1, similar enzymes: mammalian DNase III, exonuclease IV, T2- and T4-induced exodeoxyribonucleases), exodeoxyribonuclease (phage sp3-induced) (E.C. 3.1.11.4, exodeoxyribonuclease V (E.C. 3.1.11.5, similar enzyme: *Haemophilus influenzae* ATP-dependent DNase), exodeoxyribonuclease VII (E.C. 3.1.11.6, similar enzyme: *Micrococcus luteus* exonuclease), exoribonuclease II (E.C. 3.1.13.1, similar enzymes: RNase Q, RNase BN, RNase PIII, RNase Y), venom exonuclease (E.C. 3.1.15.1, similar enzymes: hog kidney phosphodiesterase, Lactobacillus exonuclease), spleen exonuclease (E.C. 3.1.16.1, similar enzymes: *Lactobacillus acidophilus* nuclease, *B subtilis* nuclease, salmon testis nuclease), deoxyribonuclease IV (phage T4-induced) (E.C. 3.1.21.2, similar enzymes: DNase V (mammalian, *Aspergillus sojae* DNase, *B subtilis* endonuclease, T4 endonuclease III, T7 endonuclease I, Aspergillus DNase K2, Vaccinia virus DNase VI, yeast DNase, Chlorella DNase), Aspergillus deoxyribonuclease K1 (E.C. 3.1.22.2, Aspergillus nuclease S1 (E.C. 3.1.30.1, similar enzymes: *N crassa* nuclease, mung bean nuclease, *Penicillium citrinum* nuclease $P_1$). Particularly preferred nucleases are nuclease $P_1$ and nuclease $S_1$ which have a relatively broad specificity against single-stranded DNA and RNA.

Where the hybrid binding reagent is an antibody, this may be obtained in any available manner such as conventional antiserum and monoclonal techniques. Antiserum can be obtained by well-established techniques involving immunisation of an animal, such as a mouse, rabbit, guinea pig or goat, with an appropriate immunogen. The immunoglobulins can also be obtained by somatic cell hybridisation techniques, also involving the use of an appropriate immunogen. The antibody reagent may also be a recombinant antibody, a chimeric antibody, or a single chain antibody. The antibody may be specific for RNA-DNA hybrids, DNA-DNA hybrids or RNA-RNA hybrids. An example of the production of anti-DNA-RNA monoclonal antibodies is given by Fliss et al. (*Applied and Environmental Microbiology* (1993) 59: 2698–2705). Antibodies specific for double-stranded nucleic acid may also be obtained from commercial sources. In preferred embodiments the antibody is labelled with either a detectable moiety or an immobilisable moiety. The covalent attachment of the label may be achieved by a number of well-known methods using a wide range of heterobifunctional reagents. For example, the method of Carlsson et al. (*Biochem J* (1978) 173: 723–737) may be used: the label is reacted with 3-[(2)-pyridyldithio] propionic acid N-hydroxysuccinimide ester (SPDP) to give a 2-pyridyl disulphide-activated label. This is mixed with an IgG antibody, and a disulphide exchange reaction yields a labelled antibody conjugate. Other approaches for labelling the antibody will be apparent to one skilled in the art. Preferred labels include the enzymes alkaline phosphatase, peroxidase, b-galactosidase, and nuclease $P_1$; the haptens digoxin and digoxigenin, and biotin or biotin analogues. In a particularly preferred embodiment the antibody is immobilised directly onto a microtitre plate. This may be achieved by a number of means well known to those skilled in the art. For example, Immulon II microtitre plates may be coated with the antibody by incubating them with the antibody dissolved in 60 mM carbonate buffer pH 9.6. Other approaches will be apparent to one skilled in the art.

Particularly attractive applications, which illustrate the operation of the present invention, are described below.

Referring now to FIG. 1, which shows three particularly preferred embodiments of the present invention, the first row shows the target nucleic acid (2), denatured if necessary to render it single-stranded, being contacted under hybridisation conditions with a nucleic acid probe (4) having a sequence complementary to at least part of the target nucleic acid and labelled at its 5'-end with an enzyme reagent (6), preferably nuclease $P_1$. In two embodiments, shown in the 2nd and 3rd columns, nucleic acid probe (4) is additionally labelled at its 3'-end with a first member of a specific binding pair (8), preferably biotin.

In the second row of FIG. 1, the pH of the mixture is adjusted to allow enzyme reagent (6) to remove single-stranded nucleic acids. These single-stranded nucleic acids comprise unhybridised probe and unhybridised target.

In the final row of FIG. 1, an sbm (10) immobilised on a solid surface (12) recognises and binds to the hybrids which have formed. Sbm (10) is preferably an antibody specific for double-stranded nucleic acid, as shown in columns 1 and 2 of FIG. 1, or streptavidin as shown in column 3. In one embodiment, shown in column 2, a second member of a specific binding pair labelled with a detection enzyme (14), preferably biotinylated alkaline phosphatase is also introduced. Unbound materials are washed off and the amount of bound probe nucleic acid-target nucleic acid-antibody complex is determined by measuring the amount of product (16) produced by enzyme label (6 or 14), preferably using an amplification assay for the nuclease $P_1$, as shown in columns 1 and 3, or alkaline phosphatase, as shown in column 2, attached to the probe.

In FIG. 1, the nuclease $P_1$ is shown to be joined directly to the nucleic acid probe. Embodiments are envisaged in which the probe is labelled with a moiety, such as flourescein isothiocyanate, and nuclease $P_1$ is attached thereto by means of an anti-FITC antibody labelled with nuclease $P_1$.

Other embodiments of the invention employing the principles described above will be obvious to one skilled in the arts. Thus the method may be applied to hybridisation and detection in solution. The target nucleic acid, denatured if necessary to render it single-stranded, is contacted under hybridisation conditions with a nucleic acid probe having a sequence complementary to at least part of the target nucleic acid and labelled with an enzyme reagent. The pH of the mixture is adjusted to allow the enzyme reagent to remove single-stranded nucleic acids, and hybrids which have formed bind to a sbm specific for the hybrid or a moiety present on the nucleic acid probe. These reactions will result in a large complex which may be detected, for example by a turbidimetric assay.

In another further application, the method may be applied to the detection of sbm-nucleic acid complexes on a solid phase. Complexes formed between a nucleic acid probe and a target nucleic acid in which either the nucleic acid probe or the target nucleic acid is immobilised on a solid phase can be detected by the method of the present invention. The pH of the mixture is adjusted to allow the enzyme reagent to remove single-stranded nucleic acids from the immobilised complex, and detection can be performed either directly using a sbm conjugated to an enzyme, a fluorescent marker or another signal generating system, or indirectly using one of the detection systems commonly used for detecting sbm's bound to their target. The solid includes nylon or nitrocellulose membranes (Southern or Northern blots), a tissue section (in situ hybridisation), or a plastic surface (an ELISA format). This approach has the advantage that the extensive washing procedures normally used in these assays can be reduced to a minimum as single-stranded nucleic acid probe will be hydrolysed by the enzyme reagent.

In a further application, the method may be applied to biosensor systems. One example of dynamic reaction detection using a biosensor surface is the surface plasmon resonance (SPR) detection system, such as that employed by the BIAcore™ biosensor system (Pharmacia). The interaction of biomolecules with an immobilised ligand on a sensor chip is measured at the surface using evanescent light. The system includes a sensor chip to which the ligand can be immobilised in a hydrophilic dextran matrix, a miniaturised fluidics cartridge for the transport of anaiytes and reagents to the sensor surface, a SPR detector, an autosampler and system control and evaluation software. Specific ligands are covalently immobilised to the sensor chip through amine, thiol or aldehyde chemistry or biospecifically by e.g. biotin-avidin interaction. An sbm specific for the hybrid or a moiety present on the nucleic acid probe is coupled to the dextran layer of a sensor chip used in the BIAcore™ biosensor-system (or other types of biosensor systems). A sample containing target nucleic acid, denatured if necessary to render it single-stranded, is contacted under hybridisation conditions with a nucleic acid probe labelled with an enzyme so that a complex is formed. The pH of the mixture is adjusted to allow the enzyme reagent to hydrolyse single-stranded nucleic acids. The sample is passed through the flow system of the BIAcoreTM and the sbm coupled to the dextran surface will bind the nucleic acid probe-target nucleic acid complex if present. Based on the SPR detection employed by the BIAcore™ this binding will generate a signal dependent on the amount of target material in the sample which becomes bound to the surface.

In a yet further application, the method may be applied to the detection of bound nucleic acid probe in cells. Under suitable conditions, nucleic acid probe oligomers may be able to penetrate the cell-wall of living or fixed cells, such as cell-lines, hemopoetic cells, and animal/human tissues. Labelling the nucleic acid probe with haptens or other reporter molecules can inhibit penetration into the cells. After the pH of the mixture is adjusted to allow the enzyme to remove single-stranded nucleic acid, hybrids formed between the nucleic acid probe and target nucleic acid are detected, either by immunohistochemistry (in frozen or fixed tissue biopsies) or by flow-cytometry (e.g. on cells treated with detergent, acetone or alcohol), or in an in vivo set up to detect binding and/or tissue distribution of nucleic acid probe's added to a cell culture or administered to a living animal.

In another application, the method may be applied to hybridisation and detection of multiple targets in a single sample solution. The target nucleic acids, denatured if necessary to render them single-stranded, are contacted under hybridisation conditions with corresponding labelled nucleic acid probes having sequences complementary to at least part of the respective target nucleic acids and which are labelled with an enzyme reagent. The pH of the mixture is adjusted to allow the enzyme reagent to remove single-stranded nucleic acids, and hybrids which have formed bind to an immobilised sbm specific for the hybrid or a moiety present on the nucleic acid probe. Unbound materials are washed away. The captured hybrids may be detected in several ways. In one approach, each set of probes used are labelled with different fluorescent or absorbing moieties. These may be interrogated at different wavelengths, and the amounts of each target present in the original sample are thereby determined. In another approach, each set of probes used are labelled with different enzymes. After treatment with the enzyme reagent, aliquots of the solution are dispensed into different wells of a microtitre plate coated with sbm soecific for the hybrid or a moiety present on the nucleic acid probe. After washing to remove unbound components, different detection reagents are added to each of the wells, and the amounts of each target present in the original sample are thereby determined.

A kit for carrying out the described methods according to the present invention contains a sbm specific for the hybrid or a moiety present on the nucleic acid probe in labelled or unlabelled form, a nucleic acid probe that is complementary to the target nucleic acid to be detected and which is labelled with an enzyme reagent specific for single-stranded nucleic acids, and a detection system.

In a preferred embodiment, the kit contains a sbm specific for the hybrid or a moiety present on the nucleic acid probe immobilised in the wells of a microtitre plate, a nucleic acid probe that is complementary to the target nucleic acid to be detected and which is labelled with an enzyme reagent specific for single-stranded nucleic acids, and a detection system.

The following examples illustrate various further aspects of the operation of the invention. These examples are not intended to limit the invention in any way.

EXAMPLE 1

Standardisation of Nuclease $P_1$

Nuclease $P_1$ (1 mg; obtained from Sigma Chemical Company, batch no: 107F0799) was dissolved in 1 ml of water to give a concentration of 22.7 $\mu$M and stored at 4° C. The activity of this solution was assayed in the following mixture: 0.16 mM NADH, 1 mM ATP, 1 mM PEP, 1 mM $MgSO_4$, 20 mM KCl, 0.5 mM adenosine 3',5'-bisphosphate, 1 U pyruvate kinase, 1 U lactate dehydrogenase and 1 U myokinase in 50 mM HEPES buffer, pH 7.2, in a total volume of 1 ml. From the change in absorbance at 340 nm the activity of nuclease $P_1$ was solution was found to be 320 U/ml, assuming a molar extinction coefficient of 6220 for NADH.

EXAMPLE 2

Amplification Assay of Nuclease $P_1$ and Nuclease $S_1$

Figure 2:
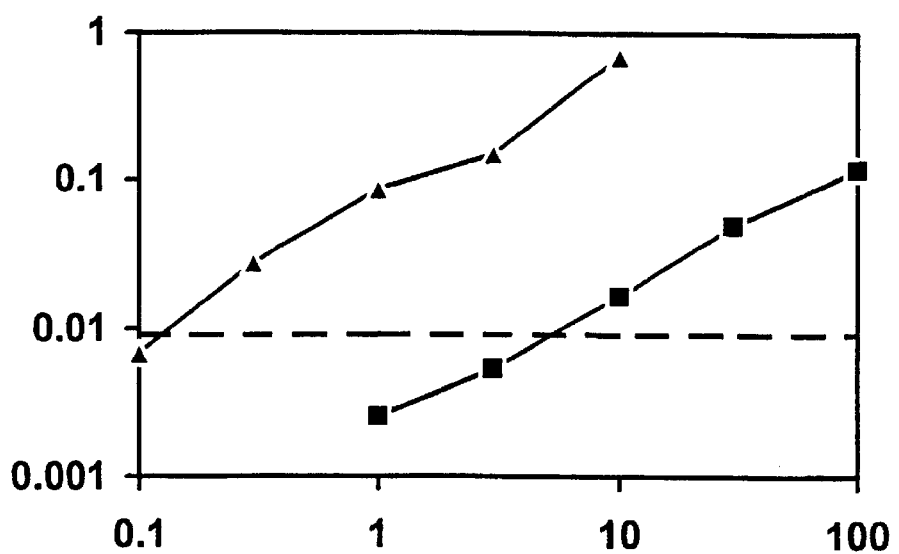
FIG. 2 shows a standard curve for the 3'FADP-based enzyme amplification assay of nuclease $P_1$ (filled triangles) and nuclease $S_1$ (filled squares). The abscissa represents the amount of each enzyme present in amol ($10^{31-18}$ mol), and the ordinate represents the absorbance obtained after 15 mins incubation at 25° C. after subtraction of the blank reading. Both scales are logarithmic. The dotted line represents the detection limit.

A solution of nuclease $P_1$ standardised according to Example 1 was serially diluted in 50 mM citrate buffer adjusted to pH 6.5 with NaOH. The assay mixture contained 20 mM 3'FADP, 0.1 mM 4-aminoantipyrine, 2 mM DHSA, 1 µg horseradish peroxidase, 0.1 M glucose and 0.1 µM apoglucose oxidase in a total volume of 0.1 ml. The change in absorbance was monitored at 520 nm in a Dynatech MR7000 plate reader fitted with a thermostatically controlled plate holder set to 25° C. FIG. 2 shows the performance of the nuclease $P_1$ assay. After a 15 minute assay period, the detection limit (defined as 3 times the standard deviation of the background reading) was 0.2 amol. Nuclease S1 was assayed in a similar manner, and the detection limit was 4 amol (FIG. 2).

EXAMPLE 3

Oligonucleotide Synthesis

Oligonucleotides were synthesised on a Cyclone™ DNA synthesiser using the Expedite™ chemistry.

The DNA to be labelled with nuclease $P_1$ was complementary to a region in the middle of the ribonuclease gene containing the K66E mutation. This probe was derivatised at the 5' end with a trityl-hexyl thiol group to facilitate linkage to nuclease $P_1$. The sequence was:

5'-GGTCACCTGCGAAAACGGGCAGG-3', SEQ ID NO: 1

Another oligonucleotide specific for repeat regions of the genomic DNA of *Streptococcus pneumoniae* (SEQ ID No 6 of U.S. Pat. No. 5,656,432) and having the sequence:

5'-TATYYACARYSTCAAAAYAGTG-3', SEQ ID NO: 2 and having a biotinylated 5'-end and an FITC-labelled 3'-end was obtained from Cruachem Ltd.

The oligonucleotides were freeze-dried and stored at 4° C. until required.

EXAMPLE 4

Derivatisation of Nuclease $P_1$

Nuclease $P_1$ (5 mg) was dissolved in 0.5 ml 0.1 M sodium bicarbonate pH 7.5 containing 0.1 M sodium chloride and desalted by gel filtration on Sephadex G25 (NAP-5 column, Pharmacia) equilibrated with the same buffer. This enzyme solution was incubated with a 50-fold molar excess of 3-(2)-pyridyldithio)-propionic acid N-hydroxysuccinimide ester (SPDP) at room temperature for 30 minutes. Unreacted SPDP was removed by gel filtration on Sephadex G25 (NAP 10 column, Pharmacia) equilibrated with the bicarbonate buffer. The 2-pyridyl disulphide-activated nuclease $P_1$ was stored at 4° C.

EXAMPLE 5

Conjugation of Nuclease $P_1$ to an Oligonucleotide

Nuclease $P_1$ was linked to 2-pyridyl disulphide as described in Example 4 and stored in 0.1 M sodium bicarbonate, pH 7.5, containing 0.1 M sodium chloride at 4° C. The K66E oligonucleotide of Example 3 was dissolved in 0.5 ml 0.1 M sodium bicarbonate buffer, pH 7.5, containing 0.1 M sodium chloride to give a final concentration of 0.36 µM. This was incubated with activated nuclease $P_1$ prepared according to Example 4 at a mole ratio of 1:2 at room temperature for 45 minutes, followed by an incubation at 4° C. for 16 h.

The conjugate was transferred to 20 mM bis-Tris propane cuffer, pH 7.5, containing 1 mM CHAPS by chromatography on Sephadex G25, and purified by ion-exchange chromatography on a Pharmacia Mono Q column. A sodium chloride gradient in the same buffer was used applied to the column and the conjugate was eluted at a molar concentration of 0.25 M.

EXAMPLE 6

Hybridisation and Detection of Plasmid DNA on Antibody-Coated Plates 50 pg of λDNA, dissolved in 95 µl sterile water, which serves as a control for non-complementary binding, is mixed with a further 5 µl of a known amount of the plasmid containing the human RNase mutant and 10 µl M sodium hydroxide in a microtitre plate well. This mixture is incubated at room temperature for 10 minutes to denature the plasmid before neutralisation with 8 µl of 0.5 M sodium citrate buffer, pH 3.0, containing 2.21 M sodium chloride and 0.1% Tween 20. 50 µl (34 fmol) of the nuclease $P_1$-conjugated reporter probe, prepared according to Example 5, dissolved in 0.1 M Tris-HCl buffer, pH 7.5, containing 7 mM zinc sulphate, 1% (w/v) PVP, 0.1 N-lauroylsarkosine and 150 mM sodium chloride, is added to each well. After hybridisation at 40° C. for 1 hour, the pH is adjusted to about 6.0 by the addition of citrate buffer, and the temperature maintained at 40° C. for 10 minutes, after which time more than 95% of unhybridised reporter probe will be hydrolysed.

The mixture is then added to a commercial microtitre plate coated with anti-double stranded DNA antibodies. After incubation at 37° C., the plates are washed 6 times with 20 mM Tris-HCl buffer, pH 7.5, containing 7 mM zinc sulphate, 1% (w/v) PVP, 0.1% N-lauroylsarkosine and 150 mM sodium chloride.

The amount of hybrid captured on the microtitre plate is quantified using the amplification assay described in Example 2.

EXAMPLE 7

Detection of *S pneumoniae* Genomic DNA

Genomic DNA from *S pneumoniae* was extracted and treated with PstI to break the DNA up into fragments. 95 µl of the treated DNA is mixed with 10 µl 1 M sodium hydroxide and incubated at room temperature for 10 minutes to denature the DNA before neutralisation with 8 µl of 0.5 M sodium citrate buffer, pH 3.0, containing 2.21 M sodium chloride and 0.1% Tween 20. 50 µl (34 fmol) of the *S pneumoniae* probe described in Example 3, dissolved in 0.1 M Tris-HCl buffer, pH. 7.5, containing 7 mM zinc sulphate, 1% (w/v) PVP, 0.1% N-laurcylsarkosine and 150 mM sodium chloride, is added, together with 50 µl of 1 µg/ml nuclease $P_1$-labelled anti-FITC antibody, prepared by linking anti-FITC antibody treated with 2-mercaptoethylamine (to yield free sulphydryl groups) with the SPDP-activated nuclease P1 of Example 4 in an analogous way to that described in Example 5. After hybridisation at 40° C. for 1 hour, the pH is adjusted to about 6.0 by the addition of citrate buffer, and the temperature maintained at 40° C. for 10 minutes, after which time more than 95% of unhybridised reporter probe will be hydrolysed.

The mixture is then added to a commercial microtitre plate coated with either anti-double stranded DNA antibodies or streptavidin. After incubation at 37° C. for 30 minutes, the plates are washed 6 times with 20 mM Tris-HCl buffer, pH 7.5, containing 7 mM zinc sulphate, 1% (w/v) PVP, 0.1% N-lauroylsarkosine and 150 mM sodium chloride.

The amount of hybrid captured on the microtitre plate is quantified using the amplification assay described in Example 2.

INDUSTRIAL APPLICABILITY

Accordingly, it will be seen that the method of the present invention can be used to detect hybrids formed between a target nucleic acid and a nucleic acid probe labelled with an enzyme reagent which removes single-stranded nucleic acid. This approach eliminates the possibility of cross-talk arising out of the binding of sbm to any single-stranded nucleic acid present. This means that the complex formed between hybrid and sbm can be detected using highly sensitive approaches, such as enzyme amplification or chemiluminescence. In addition, the nucleic acid probe may be labelled with nuclease P at each end, thereby giving an increase in the overall sensitivity of the detection reaction.

In addition to the methods described above, many other techniques for detecting the complex formed between a sbm and the hybrid will be apparent to one skilled in the art. For example the complex formed may be captured. A number of approaches are known for effecting the capture. For example, the complex may be captured by means of an antibody specific for the sbm and which is immobilised on a solid phase. Alternatively, the sbm may be labelled, and the complex captured by means of an antibody immobilised on a solid phase, and which is specific for said label. Another approach is to label the sbm with an antibody specific for a hapten or antigen immobilised on a solid support. A further approach is to label the sbm with one partner of a pair of sbm's, and capture the complex by means of the second partner immobilised on a solid surface. A yet further approach involves labelling the nucleic acid probe, and capturing the complex by means of an antibody immobilised on a solid phase which is specific for said label. Another approach is to label the nucleic acid probe with an antibody specific for a hapten or antigen immobilised on a solid support. A further approach is to label the nucleic acid probe with one partner of a pair of sbm's, and capture the complex by means of the second partner immobilised on a solid surface. Other approaches for the capture of the complex will be apparent to one skilled in the art. Unbound materials are washed off and the amount of bound probe nucleic acid-target nucleic acid-antibody complex is determined.

Again a number of approaches are known for detecting such a complex. For example, the sbm or the nucleic acid probe may be labelled with a detectable label. Alternatively, a label on the sbm or a label on the nucleic acid probe may be detected using an antibody detection system. Other approaches for the detection of the complex will be apparent to one skilled in the art.

The method has the additional advantage that it utilises a single probe, which offers cost savings and simplifies the design of assay protocols.

The method has the further advantage that it permits the detection of multiple targets in a sample, again offering economic advantage over the detection of each target singly.

Although the description above contains many specificities, these should not be construed as limiting the scope of the invention but as merely providing illustrations of some of the presently preferred embodiments of this invention. For example, the nucleic acid probe may be a peptide nucleic acid probe, or another nucleic acid analogue having modified basis or an altered backbone. When the nucleic acid probe is a peptide nucleic acid probe the enzyme reagent may be a protease specific for single stranded peptide nucleic acid.

Thus the scope of the invention should be determined by the appended claims and their legal equivalents, rather than by the examples given.

What is claimed is:

1. A method for detecting a hybrid comprising a single-stranded target nucleic acid hybridized to a nucleotide sequence complementary to said single-stranded target nucleic acid sequence, comprising the steps of;
    a) providing a nucleic acid-enzyme reagent conjugate probe, said conjugate probe comprising:
        i) a nucleotide sequence complementary to at least part of said target, and
        ii) an enzyme reagent joined to said sequence to provide said conjugate, said enzyme reagent having the activity of hydrolyzing single-stranded nucleic acids but not having the activity of hydrolyzing double-stranded nucleic acid;
    b) contacting said conjugate probe with said target under conditions of pH which are outside the activity range of said enzyme, so as to form a hybrid;
    c) adjusting said pH to a value within the activity range of said enzyme reagent by means of a base, an acid, or a buffer;
    d) hydrolyzing all or part of any single-stranded nucleic acid present by means of said enzyme reagent; and
    e) detecting said hybrid.

2. A method according to claim 1 wherein said enzyme reagent is detectable, whereby said hybrid is detected.

3. A method according to claim 1 or 2 wherein said enzyme reagent is a nuclease.

4. A method according to claim 3 wherein said nuclease is selected from the group consisting of: ribonuclease A and ribonuclease T1 in combination, exodeoxyribonuclease I (E.C. 3.1.11.1), mammalian DNase III, exonuclease IV, T2- and T4-induced exodeoxyribonucleases, exodeoxyribonuclease (phage sp3-induced) (E.C. 3.1.11.4), exodeoxyribonuclease V (E.C. 3.1.11.5), *Haemophilus influenzae* ATP-dependent DNase, exodeoxyribonuclease VII (E.C. 3.1.11.6), *Micrococcus luteus* exonuclease, exoribonuclease II (E.C. 3.1.13.1), RNase Q, RNase BN, RNase PIII, RNase Y, venom exonuclease (E.C. 3.1.15.1), hog kidney phosphodiesterase, Lactobacillus exonuclease, spleen exonuclease (E.C. 3.1.16.1), *Lactobacillus acidophilus* nuclease, *B subtilis* nuclease, deoxyribonuclease IV (phage T4-induced) (E.C. 3.1.21.2), DNase V (mammalian), *Aspergillus sojae* DNase, *B subtilis* endonuclease, T4 endonuclease III, T7 endonuclease I, Aspergillus DNase K2, Vaccinia virus DNase VI, yeast DNase, Chlorella DNase, Aspergillus deoxyribonuclease K1 (E.C. 3.1.22.2, Aspergillus nuclease S1 (E.C. 3.1.30.1), *N crassa* nuclease, mung bean nuclease, and *Penicillium citrinum* nuclease P1.

5. A method according to claim 2 wherein said enzyme reagent is nuclease P1 or nuclease S1.

6. A method according to claim 1 additionally comprising the step of contacting said hybrid with a hybrid-binding reagent.

7. A method according to claim 6 wherein said hybrid-binding reagent is an antibody specific for double-stranded nucleic acid or a DNA-binding protein specific for double-stranded nucleic acid.

8. A method according to claim 7 wherein said antibody is selected from the group consisting of monoclonal antibody, polyclonal antibody, recombinant antibody, chimeric antibody and single-chain antibody.

9. A method according to claim 6 wherein said hybrid-binding reagent is labelled.

10. A method according to claim 6 wherein said hybrid-binding reagent is immobilized.

11. A method according to claim 1 wherein said nucleic acid probe additionally comprises a first member of a specific binding pair.

12. A method according to claim 11 wherein said first member is selected from the group consisting of digoxin, digoxygenin, fluorescein, fluorescein isothiocyanate and biotin.

13. A method according to claim 11 additionally comprising the step of contacting said hybrid with a second member of a specific binding pair.

14. A method according to claim 13 wherein said second member is selected from the group consisting of anti-digoxin antibody, anti-digoxygenin antibody, anti-fluorescein antibody, anti-fluorescein isothiocyanate antibody, avidin, streptavidin and neutravidin.

15. A method according to claim 13 wherein said second member has a label.

16. A method according to claim 13 wherein said second member is immobilized.

17. A method according to claim 9 wherein said label is an immobilizable label.

18. A method according to claim 9 wherein said label is a detectable label.

19. A method according to claim 18 wherein said detectable label is selected from the group consisting of enzyme, fluorescent moiety, chemiluminescent moiety, and electrochemiluminescent moiety.

20. A method according to claim 19 wherein said enzyme is β-galactosidase or horseradish peroxidase.

21. A method according to claim 19 wherein said enzyme is selected from the group consisting of alkaline phosphatase, nuclease P1 and nuclease S1.

22. A method according to claim 5 wherein said hybrid is detected by an amplification system.

23. A method according to claim 22 wherein said amplification system comprises an apoenzyme which is convertible into a holoenzyme by interaction with an accessory subunit; and a masked form of said subunit which is convertible into its active unmasked form by the action of the said enzyme.

24. A method according to claim 23 wherein said subunit is FAD and said masked form is 3'FADP.

25. A method according to claim 23 wherein said apoenzyme is apoglucose oxidase or apo-D-aminoacid oxidase.

26. A method according to claim 1 wherein said nucleic acid probe is immobilized on a solid surface.

27. A method according to claim 1 wherein said target nucleic acid is isolated from a test sample.

28. A method according to claim 1 wherein said target nucleic acid is produced by a target amplification means.

29. A method according to claim 28 wherein said target amplification means is selected from the group consisting of polymerase chain reaction, ligase chain reaction, nucleic acid sequence-based amplification, cycling probe amplification and strand displacement amplification.

30. A method according to claim 1 wherein said target nucleic acid is selected from the group consisting of DNA, RNA or PNA.

31. A method according to claim 1 wherein said probe nucleic acid is selected from the group consisting of DNA, RNA or PNA.

32. An assay kit for detecting a single-stranded target nucleic acid comprising a nucleic acid probe complementary to the target nucleic acid to be detected which is labelled with an enzyme having the activity of hydrolyzing single-stranded nucleic acid but not having the activity of hydrolyzing double-stranded nucleic acid.

33. The assay kit according to claim 32 wherein said nuclease is selected from the group consisting of: ribonuclease A and ribonuclease T1 in combination, exodeoxyribonuclease I (E.C. 3.1.11.1), mammalian DNase III, exonuclease IV, T2- and T4-induced exodeoxyribonucleases, exodeoxyribonuclease (phage sp3-induced) (E.C. 3.1.11.4), exodeoxyribonuclease V (E.C. 3.1.11.5), *Haemophilus influenzae* ATP-dependent DNase, exodeoxyribonuclease VII (E.C. 3.1.11.6), *Micrococcus luteus* exonuclease, exoribonuclease II (E.C. 3.1.13.1), RNase Q, RNase BN, RNase PIII, RNase Y, venom exonuclease (E.C. 3.1.15.1), hog kidney phosphodiesterase, Lactobacillus exonuclease, spleen exonuclease (E.C. 3.1.16.1), *Lactobacillus acidophilus* nuclease, *B subtilis* nuclease, deoxyribonuclease IV (phage T4-induced) (E.C. 3.1.21.2), DNase V (mammalian), *Aspergillus sojae* DNase, *B subtilis* endonuclease, T4 endonuclease III, T7 endonuclease I, Aspergillus DNase K2, Vaccinia virus DNase VI, yeast DNase, Chlorella DNase, Aspergillus deoxyribonuclease K1 (E.C. 3.1.22.2, Aspergillus nuclease S1 (E.C. 3.1.30.1), *N crassa* nuclease, mung bean nuclease, and *Penicillium citrinum* nuclease P1.

34. An assay kit according to claim 32 wherein said enzyme reagent is nuclease P1 or nuclease S1.

35. An assay kit according to claim 32 additionally comprising a specific binding member specific either for hybrids formed between said single-stranded target nucleic acid and said nucleic acid probe or for a moiety present on said nucleic acid probe.

36. An assay kit according to claim 35 wherein said specific binding member is an antibody specific for double-stranded nucleic acid or a DNA-binding protein specific for double-stranded nucleic acid.

37. An assay kit according to claim 36 wherein said antibody is selected from the group consisting of monoclonal antibody, polyclonal antibody, recombinant antibody, chimeric antibody and single-chain antibody.

38. An assay kit according to claim 35 wherein said moiety is selected from the group consisting of digoxin, digoxygenin, fluorescein, fluorescein isothiocyanate and biotin.

39. An assay kit according to claim 35 wherein said specific binding member is selected from the group consisting of anti-digoxin antibody, anti-digoxygenin antibody, anti-fluorescein antibody, anti-fluorescein isothiocyanate antibody, avidin, streptavidin and neutravidin.

40. An assay kit according to claim 35 additionally comprising a detection system.

41. An assay kit according to claim 40 wherein said detection system is an amplification system.

42. An assay kit according to claim 41 wherein said amplification system comprises an apoenzyme which is convertible into a holoenzyme by interaction with an accessory subunit; and a masked form of said subunit which is convertible into its active unmasked form by the action of the said enzyme.

43. An assay kit according to claim 42 wherein said subunit is FAD and said masked form is 3'FADP.

44. An assay kit according to claim 42 wherein said apoenzyme is apoglucose oxidase or apo-D-aminoacid oxidase.

45. A conjugate molecule comprising a nucleic acid probe complementary to a target nucleic acid labeled with an enzyme having the activity of hydrolyzing single-stranded nucleic acid but not having the activity of hydrolyzing double-stranded nucleic acid.

46. The conjugate molecule of claim 45, wherein the enzyme is a nuclease selected from the group consisting of: ribonuclease A and ribonuclease T1 in combination, exodeoxyribonuclease I (E.C. 3.1.11.1), mammalian DNase III, exonuclease IV, T2- and T4-induced exodeoxyribonucleases, exodeoxyribonuclease (phage sp3-induced) (E.C. 3.1.11.4), exodeoxyribonuclease V (E.C. 3.1.11.5), *Haemophilus influenzae* ATP-dependent DNase, exodeoxyribonuclease VII (E.C. 3.1.11.6), Micrococcus luteus exonuclease, exoribonuclease II (E.C. 3.1.13.1), RNase Q, RNase BN, RNase PIII, RNase Y, venom exonuclease (E.C. 3.1.15.1), hog kidney phosphodiesterase, Lactobacillus exonuclease, spleen exonuclease (E.C. 3.1.16.1), *Lactobacillus acidophilus* nuclease, *B subtilis* nuclease, deoxyribonuclease IV (phage T4-induced) (E.c. 3.1.21.2), DNase V (mammalian), *Aspergillus sojac* DNase, *B subtilis* endonuclease, T4 endonuclease III, T7 endonuclease I, Aspergillus DNase K2, Vaccinia virus DNase VI, yeast DNase, Chlorella DNase, Aspergillus deoxyribonuclease K1 (E.C. 3.1.22.2), Aspergillus nuclease S1 (E.C. 3.1.30.1), *N crassa* nuclease, mung bean nuclease, and *Penicillium citrinum* nuclease P1.

47. The conjugate molecule of claim 45, wherein said enzyme reagent is nuclease P1 or nuclease S1.

48. The conjugate molecule of claim 45, further comprising a specific binding member specific either for hybrids formed between said single-stranded target nucleic acid and said nucleic acid probe or for a moiety present on said nucleic acid probe.

49. The conjugate molecule of claim 48, wherein said specific binding member is an antibody specific for double-stranded nucleic acid or a DNA binding protein specific for double-stranded nucleic acid.

50. The conjugate molecule of claim 49, wherein said antibody is selected from the group consisting of monoclonal antibody, polyclonal antibody, recombinant antibody, chimeric antibody, and single-chain antibody.

51. The conjugate molecule of claim 48, wherein said moiety is selected from the group consisting of digoxin, digoxygenin, fluorescein, fluorescein isothiocyanate and biotin.

52. The conjugate molecule of claim 48, wherein said specific binding member is selected from the group consisting of anti-digoxin antibody, antidigoxygenin antibody, anti-fluorescein antibody, anti-fluorescein isothiocyanate antibody, avidin, streptavidin, and neutravidin.

53. A method for making a nucleic acid probe and enzyme reagent conjugate, comprising: synthesizing an oligonucleotide of a desired sequence; providing an enzyme reagent having the activity of hydrolyzing single-stranded nucleic acids but not having the activity of hydrolyzing double-stranded nucleic acid; and linking said sequence and said enzyme to form said conjugate.

54. The method of claim 53, wherein the enzyme is a nuclease selected from the group consisting of: ribonuclease A and ribonuclease Ti in combination, exodeoxyribonuclease I (E.C. 3.1.11.1), mammalian DNase III, exonuclease IV, T2- and T4-induced exodeoxyribonucleases, exodeoxyribonuclease (phage sp3-induced) (E.C. 3.1.11.4), exodeoxyribonuclease V (E.C. 3.1.11.5), *Haemophilus influenzae* ATP-dependent DNase, exodeoxyribonuclease VII (E.C. 3.1.11.6), *Micrococcus luteus* exonuclease, exoribonuclease II (E.C. 3.1.13.1), RNase Q, RNase BN, RNase PIII, RNase Y, venom exonuclease (E.C. 3.1.15.1), hog kidney phosphodiesterase, Lactobacillus exonuclease, spleen exonuclease (E.C. 3.1.16.1), *Lactobacillus acidophilus* nuclease, *B subtilis* nuclease, deoxyribonuclease IV (phage T4-induced) (E.c. 3.1.21.2), DNase V (mammalian), *Aspergillus sojac* DNase, *B subtilis* endonuclease, T4 endonuclease III, T7 endonuclease I, Aspergillus DNase K2, Vaccinia virus DNase VI, yeast DNase, Chlorella DNase, Aspergillus deoxyribonuclease K1 (E.C. 3.1.22.2), Aspergillus nuclease S1 (E.C. 3.1.30.1), *N crassa* nuclease, mung bean nuclease, and *Penicillium citrinum* nuclease P1.

55. The method of claim 53, wherein said enzyme reagent is nuclease P1 or nuclease S1.

56. The method of claim 53, further comprising the step of linking a specific binding member, specific either for hybrids formed between said single-stranded target nucleic acid and said nucleic acid probe or for a moiety present on said nucleic acid probe, to form a conjugate further comprising said specific binding member.

57. The conjugate molecule of claim 56, wherein said specific binding member is an antibody specific for double-stranded nucleic acid or a DNA binding protein specific for double-stranded nucleic acid.

* * * * *